United States Patent [19]

Naik et al.

[11] Patent Number: 5,776,977

[45] Date of Patent: Jul. 7, 1998

[54] ARYLCYCLOALKYL DERIVATIVES, THEIR PRODUCTION AND THEIR USE

[75] Inventors: Ramachandra Ganapati Naik; Vilas Narayan Mumbaikar; Rangarajan Vasumathy; Aftab Dawoodbhai Lakdawala, all of Bombay; Mandakini Vithalrao Shirole, Thane; Bansi Lal, Bombay, all of India; Jürgen Blumbach, Niedernhausen, Germany; Klaus Ulrich Weithmann, Hofheim am Taunus, Germany; Robert Ryder Bartlett, Darmstadt, Germany

[73] Assignee: Hoechst Aktiengesellschaft, Frankfurt am Main, Germany

[21] Appl. No.: 692,129

[22] Filed: Aug. 5, 1996

Related U.S. Application Data

[62] Division of Ser. No. 444,518, May 19, 1995, Pat. No. 5,589,514, which is a continuation of Ser. No. 2,863, Jan. 14, 1993, abandoned.

[30] Foreign Application Priority Data

Jan. 16, 1992 [EP] European Pat. Off. .......... 92 100 664

[51] Int. Cl.$^6$ .................... A61K 31/235; A61K 31/215; C07C 65/32; C07C 69/84
[52] U.S. Cl. .................. 514/532; 514/533; 514/534; 514/539; 514/541; 514/544; 514/545; 514/547; 560/21; 560/23; 560/37; 560/42; 560/51; 560/53; 560/59; 560/64; 560/102; 560/118; 560/126; 562/459
[58] Field of Search .................. 514/532, 533, 514/534, 539, 541, 544, 547; 560/51, 53, 59, 64, 102, 118, 126

[56] References Cited

U.S. PATENT DOCUMENTS

| | | | |
|---|---|---|---|
| 4,225,619 | 9/1980 | Brickl et al. | 424/331 |
| 4,900,727 | 2/1990 | Kattige et al. | 514/212 |

FOREIGN PATENT DOCUMENTS

| | | |
|---|---|---|
| 0 150166A | 1/1984 | European Pat. Off. . |
| 0 241 003 | 10/1987 | European Pat. Off. . |
| 0 292 576 | 6/1988 | European Pat. Off. . |
| 2 602 228 | 2/1988 | France . |
| 61-26775 | 2/1986 | Japan . |
| 61-144717 | 6/1986 | Japan . |
| 61-167288 | 7/1986 | Japan . |
| 61-248389 | 10/1986 | Japan . |
| 62-142166 | 6/1987 | Japan . |
| 62-281022 | 11/1987 | Japan . |

*Primary Examiner*—Johann Richter
*Assistant Examiner*—Jane Oswecki
*Attorney, Agent, or Firm*—Finnegan, Henderson, Farabow, Garrett & Dunner, L.L.P.

[57] ABSTRACT

Compounds of formula I,

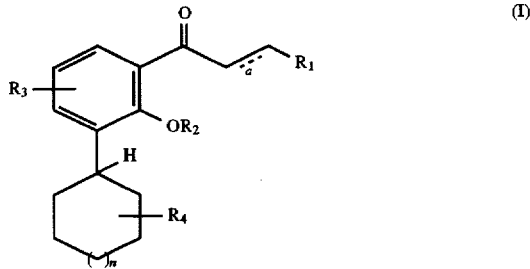

wherein the substituents $R_1$–$R_4$ and a have the given meanings and show an activity against inflammatory conditions.

9 Claims, 1 Drawing Sheet

ARYLCYCLOALKYL DERIVATIVES, THEIR PRODUCTION AND THEIR USE

This application is a division of Ser. No. 08/444,518 filed May 19, 1995, now U.S. Pat. No. 5,589,514 which is a file wrapper continuation of Ser. No. 08/002,863 filed Jan. 14, 1993, abandoned.

The present invention relates to novel arylcycloalkyl derivatives, their production, and their use.

The chalcones of the following general formula Ia are known by the following prior art:

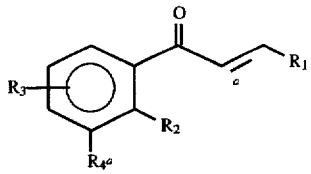

1. J.P. 281022—Compounds of formula Ia, wherein
$R_1$=substituted phenyl,
$R_2$=OH,
a=single or double bond,
$R_3$=OH,
$R_{4_a}$=H, isoprenyl or isopentyl,
and are effective in treatment of diseases caused by hypersecretion of androgens, e.g., prostatomegaly, alopecia in males, acne vulgaris or seborrhoea.

2. J.P. 026775—Compounds of formula Ia wherein
$R_1$=substituted phenyl,
$R_2$=H, OH, acetoxy, carboxymethoxy or methoxycarbonylmethoxy,
$R_3$=OH, methoxy, benzyloxy, H,
$R_{4_a}$=H, isoprenyl or isopentyl,
and possess anti-hyaluronidase activity.

3. J.P. 142166—Compounds of formula Ia wherein
$R_1$=substituted phenyl,
$R_2$=OH, acetoxy, carboxymethoxy, methoxycarboxylmethoxy,
$R_3$=OH, methoxy, H,
a=single or a double bond,
$R_{4_a}$=isoprenyl, isopentyl, n-propyl or H,
and are useful as aldose reductase inhibitors—used to treat diabetic complications such as cataracts, retinitis, nerve disorder or kidney disease.

4. J.P. 248389—Compounds of formula Ia wherein
$R_1$=substituted phenyl,
$R_2$=OH,
$R_3$=OH,
a=a double bond,
$R_{4_a}$=H,
and are useful as aldose reductase inhibitors—for treatment of diabetes mellitus complications.

5. J.P. 144717—Compounds of formula Ia wherein
$R_1$=substituted phenyl,
$R_2$=H or OH,
$R_3$=H or OH,
a=a double bond,
$R_{4_a}$=H or OH,
and are useful as c-kinase inhibitors and antitumor agents.

6. EP 150166—Compounds of formula Ia wherein
$R_1$=substituted phenyl $R_2$=H, halogen, lower alkyl, lower alkoxy, CN, carboxy, nitro,
$R_3$=H, halogen, lower alkyl, lower alkoxy, CN, carboxy, nitro, hydroxy, substituted acetic acid derivative,
a=a double bond,
$R_{4_a}$=as in $R_3$
and having inhibitory effect on hydroxy-prostaglandin dehydrogenase. They may have potential local activity against gastrointestinal disorders such as gastric ulcer, and ulcerative colitis. Other potential fields of application include the treatment of rheumatoid arthritis, circulatory disorders, cancer, lack of fertility and cell regulation.

7. J.P. 167288—Compounds of formula Ia wherein
$R_1$=substituted phenyl,
$R_2$=H,
$R_3$=OH,
a=a single bond,
$R_{4_a}$=OH,
and are selective inhibitors of 5-lipoxygenase and have excellent anti-allergic activity, thus are useful as a safe anti-allergic drug such as antiasthmatic, antiphlogistic and immune activating drug.

The present invention relates to compounds of formula I, wherein

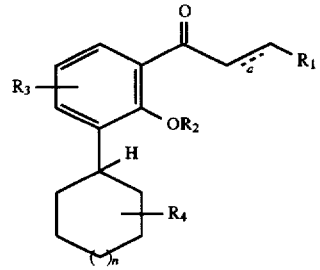

$R_1$=$C_1$-$C_6$-alkyl, substituted $C_1$-$C_6$-alkyl, C(O)O—$C_1$-$C_4$-alkyl, C(O)OH, or a residue selected from

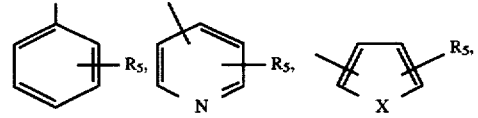

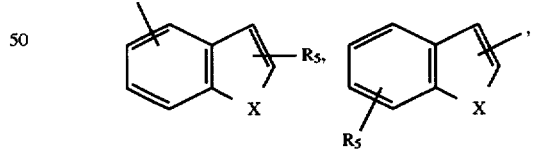

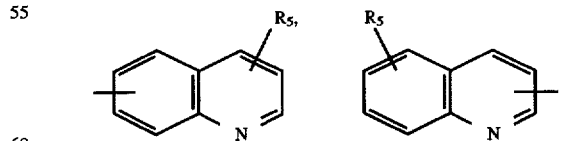

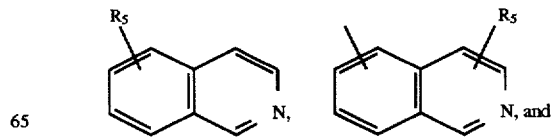

-continued

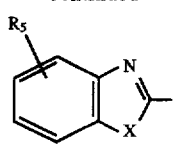

wherein R₅ is one, two, three, or four of the residues which are independent of each other and are selected from the group consisting of H, $C_1$–$C_6$-alkyl, substituted $C_1$–$C_6$-alkyl, hydroxy, $C_1$–$C_6$-alkoxy, carboxy, cyano, NHC(O)$C_1$–$C_3$-alkyl, —O$C_1$–$C_3$-alkyl-phenyl, —OCH₂—O—, $C_1$–$C_4$-alkyl—O—$C_1$–$C_4$-alkyl, —O—C(O)—$C_1$–$C_4$-alkyl, —C(O)—O—$C_1$–$C_4$-alkyl, halogen, amino, nitro, —NH—$C_1$–$C_4$-alkyl, —N—($C_1$–$C_4$-alkyl)₂, and —$C_1$–$C_4$-alkyl-$R_6$ wherein $R_6$ is a residue selected from

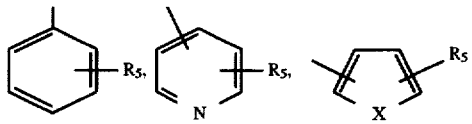

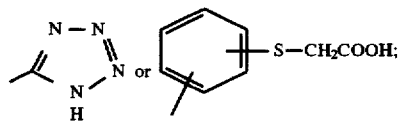

X is O, S, N—H, N—$C_1$–$C_6$-alkyl;

R₂ is H, $C_1$–$C_6$-alkyl, —C(O)—$C_1$–$C_6$-alkyl;

R₃ is one, two, or three of the residues which are independent of each other and are selected from the group consisting of H, $C_1$–$C_6$-alkyl, —C(O)—$C_1$–$C_6$-alkyl, —C(O)—O—$C_1$–$C_6$-alkyl, OH, O—$C_1$–$C_6$-alkyl, —O—C(O)—$C_1$–$C_6$-alkyl, halogen;

R₄ is H, —OH, —O—$C_1$–$C_6$-alkyl, —O—C(O)—$C_1$–$C_6$-alkyl, —C(O)—OH, —C(O)—O—$C_1$–$C_6$-alkyl,

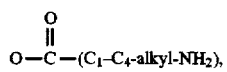

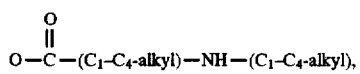

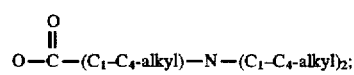

n 0, 1 or 2; and a represents an optional additional single bond.

Preferred compounds are compounds of formula II

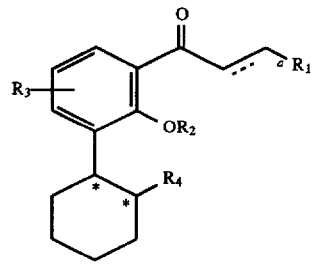

wherein $R_1$, $R_2$, $R_3$, $R_4$ and a are as previously defined.

Among this group of compounds, those are preferred in which $R_1$ is

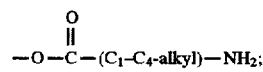

$R_5$ denoting H, $C_1$–$C_6$-alkyl, substituted $C_1$–$C_6$-alkyl, hydroxy, $C_1$–$C_3$-alkoxy, halogen, $C_1$–$C_4$-alkyl-$R_6$ wherein $R_6$ stands for

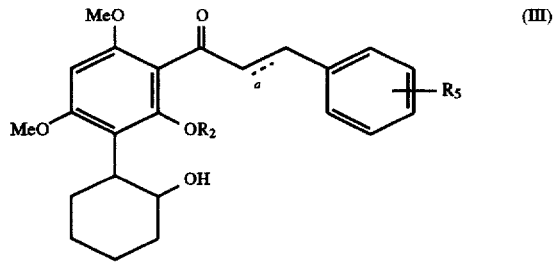

$R_4$ denotes H, OH or

—O—C(=O)—($C_1$–$C_4$-alkyl)—NH₂;

X stands for O, NH, S, N—$C_1$–$C_6$-alkyl; and
a stands for an optional additional bond.
Particularly preferred are compounds of formula III (III)

wherein
$R_2$ is H or $C_1$–$C_3$-alkyl,
$R_5$ denotes one or two halogens or one or two $C_1$–$C_6$-alkyl or $C_1$–$C_3$-alkoxy groups, and a denotes an optional additional single bond.

The above term substituted alkyl means alkyl, preferably $C_1$–$C_3$-alkyl, substituted by preferably one halogen, hydroxy, $C_1$–$C_3$-alkoxy, amino, $C_1$–$C_4$-alkylamino, di-($C_1$–$C_4$-alkyl)-amino, carbonyl or carboxy-$C_1$–$C_4$-alkyl.

The compounds of the invention contain two asymmetric centers, designated with asterisks in formula II, at the points of attachment of $R_4$, (e.g., formula II, when $R_4$=H) and of the aryl group on the carbocyclic ring; therefore, four isomers are possible, designated individually as the cis-(+), cis-(−), trans (+), and trans-(−) forms. The present invention includes each of the four isomers individually or as mixtures of two or more of the four isomers.

Examples of Particularly Preferred Compounds are 1. trans-(+/−)-2-[4,6-Dimethoxy-2-hydroxy-3(3-(4-chlorophenyl))prop-2-enoyl]-phenylcyclohexanol.
2. trans-(+/−)-2-[4,6-Dimethoxy-2-hydroxy-3(3-(2-chlorophenyl))prop-2-enoyl]-phenylcyclohexanol.
3. trans-(+/−)-2-[4,6-Dimethoxy-2-hydroxy-3(3-(3-chlorophenyl))prop-2-enoyl]-phenylcyclohexanol.
4. trans-(+/−)-2-[4,6-Dimethoxy-2-hydroxy-3(3-(2-bromophenyl))prop-2-enoyl]-phenylcyclohexanol.
5. trans-(+/−)-2-[4,6-Dimethoxy-2-hydroxy-3(3-(3-bromophenyl))prop-2-enoyl]-phenylcyclohexanol.
6. trans-(+/−)-2-[4,6-Dimethoxy-2-hydroxy-3(3-(4-bromophenyl))prop-2-enoyl]-phenylcyclohexanol.
7. trans-(+/−)-2-[4,6-Dimethoxy-2-hydroxy-3(3-(4-fluorophenyl))prop-2-enoyl]-phenylcyclohexanol.
8. trans-(+/−)-2-[4,6-Dimethoxy-2-hydroxy-3(3-(2-methylphenyl))prop-2-enoyl]-phenylcyclohexanol.
9. trans-(+/−)-2-[4,6-Dimethoxy-2-hydroxy-3(3-(4-methylphenyl))prop-2-enoyl]-phenylcyclohexanol.
10. trans-(+/−)-2-[4,6-Dimethoxy-2-hydroxy-3(3-(2,3-dichlorophenyl))prop-2-enoyl]-phenylcyclohexanol.
11. trans-(+/−)-2-[4,6-Dimethoxy-2-hydroxy-3(3-(2,6-dichlorophenyl))prop-2-enoyl]-phenylcyclohexanol.
12. trans-(+/−)-2-[4,6-Dimethoxy-2-hydroxy-3(3-(2,6-dichlorophenyl))prop-2-enoyl]-phenylcyclohexanol.
13. trans-(+)-2-[4,6-Dimethoxy-2-hydroxy-3-(3-(4-chlorophenyl))prop-2-enoyl]phenylcyclohexanol.
14. trans-(−)-2-[4,6-Dimethoxy-2-hydroxy-3-(3-(4-chlorophenyl))prop-2-enoyl]phenylcyclohexanol.
15. trans-(+/−)-2-[4,6-Dimethoxy-2-hydroxy-3-(3-(3-methoxyphenyl))prop-2-enoyl]phenylcyclohexanol.
16. trans-(−)-2-[4,6-Dimethoxy-2-hydroxy-3-(3-(3-methoxyphenyl))prop-2-enoyl]phenylcyclohexanol.
17. trans-(+/−)-2-[4,6-Dimethoxy-2-hydroxy-3-(3-(4-chloro-3-nitrophenyl))prop-2-enoyl]phenylcyclohexanol.
18. trans-(−)-2-[4,6-Dimethoxy-2-hydroxy-3-(3-(4-chloro-3-nitrophenyl))prop-2-enoyl]phenylcyclohexanol.
19. trans-(+/−)-1-[4,6-Dimethoxy-2-hydroxy-3-(2-(β-amino)acetoxy)cyclohexyl]phenyl-1-(3-(3,4-dimethoxy)phenyl)propanone hydrochloride.

A further subject of the instant application is a process for the production of compounds of formula I as described above wherein a compound of formula V

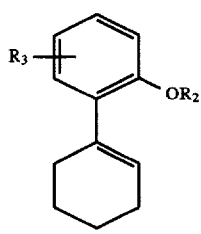

A) is converted into a compound of formula VI,

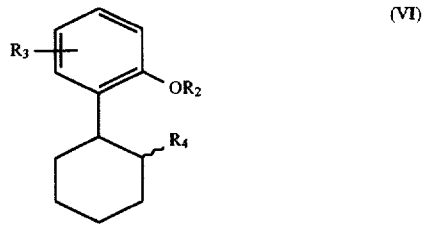

(VI)

$R_4$ denoting OH by treatment with a borane-solvent-complex followed by oxidation or B) to get a compound of formula VI, a compound of formula V is treated with a peracid and the epoxide thus produced is treated with a hydride reagent or C) the compound of formula VI is produced by condensation of a suitable arene with cyclohexene oxide in the presence of an acid catalyst and D) a compound of formula VI is treated with acetic anhydride and a mineral acid to give a compound of formula VII,

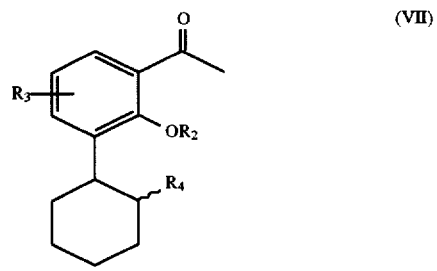

(VII)

wherein $R_2$ is methyl and $R_4$ is O—C(O)—Me and

E) a compound of formula VII as described under D) is demethylated by treatment with a Lewis acid or a demethylating agent to give a compound of formula VII wherein $R_2$ denotes H and $R_4$ denotes OC(O)Me and F) a compound of formula VII wherein $R_2$ denotes H and $R_4$ denotes OH is produced by treatment of a compound produced under E) with dilute alkali, and G) the compound of formula VII is converted into a compound of formula I (a=additional bond) by treatment with an appropriate aldehyde in the presence of a base and the compound of formula I (a=no additional bond) is produced by hydrogenation of the compound of formula I (a=additional bond), $R_1$, $R_2$ and $R_3$, where not explained explicitly, having the meaning as indicated above.

The compounds of formula V are prepared by methods known to a person skilled in the art. Typically, they are prepared by addition of aryllithiums of formula IV to cyclohexanone followed by acid catalyzed dehydration, $R_2$ and $R_3$ having the meaning as indicated above.

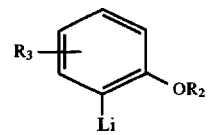

(IV)

A suitable borane-solvent complex for step A of the above sequence is, for instance, borane-tetrahydrofuran or borane dimethylsulfide. The oxidation can be carried out using alkaline hydrogen peroxide. A suitable peracid for step B is, for instance, chloroperbenzoic acid. An example of a suitable hydride reagent is lithium aluminum hydride.

Step C can be carried out using as arene, 1,3,5-trimethoxy-benzene, for example, the acid catalyst being aluminum chloride.

The mineral acid needed for step D can be, for instance, phosphoric acid.

Step E can be carried out using, for example, as Lewis acid boron tribromide and as demethylating agent, metal thiolates. The preferred dilute alkali for step F is 2N sodium hydroxide solution.

The base in the presence of which step G is carried out can be sodium hydroxide, for example.

The products according to the above reaction steps can be used for further reactions to compounds according to the instant invention. Most of said reactions can be carried out according to procedures described in European patent application 0 241 003. Additional information about starting products, intermediates and derivatization reactions can be obtained from the patent literature mentioned in the introduction.

The physical constants of some of the preferred compounds of the present invention are listed in Table 1.

TABLE 1

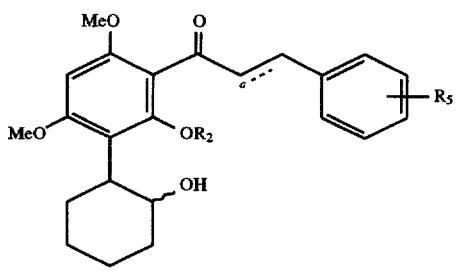

| Compound No. | $R_5$ | $R_2$ | a | m.p. °C. | Sign of Rotation |
|---|---|---|---|---|---|
| 1. | H | H | Δ2',3' | 183–185 | ± |
| 2. | 2-Cl | H | " | 204–206 | " |
| 3. | 3-Cl | H | " | 170 | " |
| 4. | 4-Cl | H | " | 221 | " |
| 5. | 2-Br | H | " | 203 | " |
| 6. | 3-Br | H | " | 171 | " |
| 7. | 4-Br | H | " | 222 | " |
| 8. | 4-F | H | " | 215–216 | " |
| 9. | 2,3-Cl$_2$ | H | " | 216 | " |
| 10. | 2,4-Cl$_2$ | H | " | 226–228 | " |
| 11. | 2,6-Cl$_2$ | H | " | 197 | " |
| 12. | 2-Me | H | " | 199 | " |
| 13. | 4-Me | H | " | 213 | " |
| 14. | 4-OMe | H | " | 210 | " |
| 15. | 4-Cl | Me | " | 175 | " |
| 16. | 4-Cl | H | H,H | 190 | " |
| 17. | 4-F | H | H,H | 169 | " |
| 18. | 3,4-Cl$_2$ | H | Δ2',3' | 202 | " |
| 19. | 3,5-Cl$_2$ | H | " | 227 | " |

TABLE 1-continued

| Compound No. | $R_5$ | $R_2$ | a | m.p. °C. | Sign of Rotation |
|---|---|---|---|---|---|
| 20. | 2-OMe | H | " | 215 | " |
| 21. | 3-OMe | | " | 178 | " |
| 22. | 3,4-(OMe)$_2$ | H | " | 194 | " |
| 23. | 2,5-(OMe)$_2$ | H | " | 185 | " |
| 24. | 2,4-(OMe)$_2$ | H | " | 224–225 | " |
| 25. | 2,4,6-(OMe)$_3$ | H | " | 162 | " |
| 26. | 4-COOH | H | " | 240 | " |
| 27. | 4-N(CH$_3$)$_2$ | H | " | 187 | " |
| 28. | 4 Cl, 3-NO$_2$ | H | " | 215 | " |
| 29. | 3-OH | H | " | 210 | " |
| 30. | 4-OH | H | " | 210 | " |
| 31. | 2-OH | H | " | 209 | " |
| 32. | 4-CF$_3$ | H | " | 177 | " |
| 33. | 4-NHCOCH$_3$ | H | " | 274 | " |
| 34. | 3,4-(OMe)$_2$ | H | H,H | 151 | " |
| 35. | 2,4,6-(OMe)$_3$ | H | H,H | 132 | " |
| 36. | 2-OH | H | H,H | 190 | " |
| 37. | 3-OH | H | H,H | 63 | " |
| 38. | 4-OH | H | H,H | 216 | " |
| 39. | 3,4-(OH)$_2$ | H | H,H | 201 | " |
| 40. | 2-CH$_3$ | H | H,H | 157 | " |
| 41. | 3,4-(OCH$_2$Ph)$_2$ | H | Δ'2,3 | 173 | " |
| 42. | 3,4-O—CH$_2$—O— | H | Δ'2,3 | 185 | " |
| 43. | 4-Cl | H | " | 231 | (+) |
| 44. | 4-Cl | H | " | 231 | (−) |
| 45. | 4-Cl,3-NO$_2$ | H | " | 235 | (+) |
| 46. | 4-Cl,3-NO$_2$ | H | " | 235 | (−) |
| 47. | 3-OMe | H | " | 191 | (+) |
| 48. | 3-OMe | H | " | 191 | (−) |
| 49. | 3,4-(OMe)$_2$ | H | " | 195 | (+) |
| 50. | 3,4-(OMe)$_2$ | H | " | 195 | (−) |
| 51. | 2,3-Cl$_2$ | H | " | 217 | (+) |
| 52. | 2,3-Cl$_2$ | H | " | 217 | (−) |

TABLE 1A

Compounds of formula II in which $R_3 = 4,6\text{-}(OCH_3)_2$

| Compound No. | $R_1$ | a | $R_2$ | | m.p. °C | Sign of Rotation |
|---|---|---|---|---|---|---|
| 1. | 2-Thienyl | $\Delta$ 2',3' | H | OH | 179–180 | (±) |
| 2. | 2-Furyl | " | H | OH | | " |
| 3. | 4-Nitrophenyl | " | H | $-OCOCH_3$ | 175 | " |
| 4. | 4-Cyanophenyl | " | H | $-OCOCH_3$ | 172 | " |
| 5. | 4-Chlorophenyl | " | H | $-OCOCH_2NH_2-HCl$ | 152 | " |
| 6. | 3,4-Dimethoxyphenyl | " | H | $-OCOCH_2NH_2-HCl$ | 136–138 | " |

The novel compounds of the present invention display interesting pharmacological activity when tested in pharmacological models; compound 4 of Table 1 will be used in the examples as a representative compound.

As shown in the examples, the instant compounds have antiinflammatory properties. The compounds are particularly useful to inhibit or antagonize the responses mediated by endogenous molecules such as lipoxygenases and/or leukotrienes, interleukins and protein kinase C. The compounds of the invention, alone or in the form of a suitable formulation, are thus useful as medicaments in the treatment of inflammatory conditions, in particular chronic inflammatory conditions such as rheumatoid arthritis, osteoarthritis, asthma and malignancies.

Accordingly, another subject of the instant invention are the use and methods of use to treat and prevent the above-mentioned inflammatory conditions by administration of an active amount of one or more compounds of the instant invention. Furthermore, pharmaceuticals containing one or more compounds as explained above are a subject of this invention. Said pharmaceuticals can be produced and administered according to methods known in the art.

The following examples as well as the patent claims further illustrate the instant invention.

EXAMPLE 1

Inhibition of Leukotriene Induced Contraction of Isolated Guinea Pig Ileum

Guinea pigs of either sex weighing 300–350 g were sensitized with a suspension of aluminum hydroxide gel and egg albumin. After 21 days, each animal was exposed to 0.5% egg albumin aerosol in an air tight perspex chamber and only those animals which developed allergic bronchoconstriction were selected for further experiment.

The animals were tested for one week after antigenic exposure and then sacrificed by head blow and cutting carotid arteries. The lung was quickly removed and placed in aerated Tyrode solution kept at 37° C. The lung was cut into uniform strips and each strip was placed in an organ bath containing isolated guinea pig ileum connected to potentiometric recorder through isotonic transducer in the presence of Tyrode solution kept at 37° C. After a stabilizing period of 30 minutes, the reactivity of ileum to histamine was confirmed by challenging it with 100 ng–200 ng/ml of histamine. The perfusion fluid was then replaced by Tyrode solution containing Atropine ($10^{-7}$M), Mepyramine maleate ($10^{-7}$M) and methylsergide ($10^{-7}$M). Three minutes later, lung strip was challenged by egg albumin (25 µg/ml) and release of leukotrienes was monitored in terms of slow contraction of ileum. The ileum was allowed to contract for 10–15 minutes when a plateau was achieved. The test compound (compound 4 of Table 1) was then added to observe the relaxation.

The specificity of leukotriene antagonism was determined by inducing contraction of guinea pig ileum with agonists like histamine, acetylcholine and KCl. Compounds having specific effect against lipoxygenase products induced contraction normally would not show any inhibition of histamine, acetylcholine and KCl induced contraction. The data are shown in Table 2.

| Conc. (M) | % Relaxation | App. $IC_{50}$ (M) |
|---|---|---|
| $1.2 \times 10^{-6}$ | 36.8 | |
| $1.68 \times 10^{-6}$ | 50.5 | $1.68 \times 10^{-6}$ |
| $2.4 \times 10^{-6}$ | 62.4 | |
| $7.2 \times 10^{-6}$ | 68.0 | |

No effect on histamine and KCl induced contraction up to $7.11 \times 10^{-5}$ M.

Compound 4 as representative of the novel compounds of the present invention inhibits the contractions induced by leukotrienes.

EXAMPLE 2

Inhibition of Cotton Pellet Granuloma in Rats

This model permits the evaluation of a compound's potential to inhibit artificially induced granuloma. The implantation of carrageenin impregnated cotton pellets results in production of large, well-defined granuloma which are easily dissected. The potency of the compounds are assessed by measuring the reduction in granuloma tissue formation.

Preparation of Saline and Carrageenin Cotton Pellets

Cotton wool pellets weighing 40 mg were used for sterilization. Half the number of pellets were dipped in saline and the remaining in 1% aqueous solution (Viscarin® type 402, Marine Colloids Inc. Springfield) until they were soaked well, then squeezed slightly to remove excess saline or carrageenin.

Pellets were dried overnight under a lamp. The pellets in the weight range of 42–44 mg were selected.

Animal Preparation

Rats (in groups of 6, male or female, Charles River, Wistar, weighing 140–150 g) were anaesthetized with ether. The back was shaved and cleaned; swabbed with alcohol and one centimeter incision was made in the lower midback.

A small channel was made bilaterally using a blunt forceps and one cotton pellet placed in each channel. Air from the incision was removed and the wound was stitched. The test compound was prepared in 0.5% carboxyl methyl cellulose and was administered orally at a dose of 10, 20 and 30 mg/kg daily for seven days. Three hours after the administration of the last dose on day 7, animals were sacrificed. The pellets were removed by cutting the skin along the dorsal midline and peeling the skin away from the bodywall in both lateral directions. The pellets were weighed and then placed in drying oven at 140° C. overnight The dry weights were then recorded and the amount of granuloma was assessed by subtracting the original pellet weight from wet weights and dry weights. The data was evaluated using the difference of left and right weights (cf. Table 3).

TABLE 3

Effect of Compound No. 4 on Cotton Pellet Granuloma in Rats.

| Treatment | Dose mg/kg, p.o. × 5 | % Inhibition of granuloma | |
|---|---|---|---|
| | | Wet wt. | Dry wt. |
| Compound No. 4 | 10 | 21 | 35.6 |
| | 20 | 54 | 89.0 |
| | 30 | 64 | 82.8 |
| Hydrocortisone | 30 | 20.5 | 37.5 |

Compound 4 as representative of the compounds of the present invention inhibits the granuloma formation induced by carrageenin.

EXAMPLE 3

Inhibition of Micro-Anaphylactic Shock of Guinea Pigs

Guinea pigs of either sex weighing between 300–350 g were sensitized with egg albumin absorbed over $Al(OH)_3$ gel. After 21 days of sensitization, each animal was placed in an air tight perspex chamber and exposed to 0.5% egg albumin aerosol through EEL atomizer. EEL atomizer was operated by connecting it to the pressurized air through water trap and dial type sphygmomanometer at the constant air pressure of 180 mm Hg. The time of onset of asthma in seconds and recovery period in minutes was noted.

Each animal was exposed to egg albumin aerosol at an interval of 15 days to maintain the consistency of the reactivity of animals to the antigen. After 3 such control exposures, animals were subjected to drug treatment. On the day of experiment one group of Guinea pigs consisting of 10 animals was kept as control exposing them only to 0.5% egg albumin aerosol. Another group of 10 guinea pigs was treated with Indomethacin 10 mg/kg i.p. 30 mins. before the exposure to the antigen. Yet another group of 10 guinea pigs was pretreated with Indomethacin 10 mg/kg i.p. and 30 mins. after Indomethacin pretreatment the test compound (20 mg/ip) was injected. Fifteen mins. after the administration of the test compound the animals were exposed to 0.5% egg albumin aerosol. Onset time of recovery period of each group was noted (cf. Table 4).

TABLE 4

Effect of Compound No. 4 on microanaphylactic shock of guinea pigs.

| Treatment | Onset Time in secs. | Recovery period in mins. |
|---|---|---|
| Control group | 75 + 8.7 | 37 + 3.4 |
| Indomethacin treated group 10 mg/kg, i.p. | 82.4 + 11.5 | 147.8 + 3.5 |
| Compound 4, 20 mg/kg$^{-1}$, i.p. present invention + pretreatment with indomethacin, 10 mg/kg, i.p. | 149.2 + 25.1 | 77.6 + 4.7 |

Compound 4 as the representative example of the novel compounds of the present invention protects the animals from bronchoconstriction induced by leukotrienes, subsequent to the exposure of egg albumin aerosol.

EXAMPLE 4

Inhibition of IL-1 Release Human Mononuclear Cells

Purification of mononuclear cells from human blood.

10 ml of human blood were carefully drawn from the antecubital vein using a syringe containing 1 ml of a solution of 3.8% sodium citrate. After dilution with 10 ml PM 16 (Serva, Heidelberg, FRG) and underlayering with 15 ml Lymphoprep® (Molter GmbH), the sample was centrifuged at 400 X g for 40 min at 20° C. The mononuclear cells forming a white ring between lymphoprep and plasma were carefully aspirated by a syringe, diluted with 1:1 with PM 16 and centrifuged again at 400 X g for 10 min. The supernatant was washed with 10 ml RPMI 1640 (Gibco, Berlin, FRG), containing additionally 300 mg/l L-glutamine, 25 mmol/l RPM 1640, containing additionally 300 mg/l L-glutamine, 25 mmol/l HEPES, 100 µg/ml streptomycin and 100 µg/ml penicillin. Finally, using a Coulter counter IT, the cell suspension was adjusted to $5 \times 10^6$ cells/ml. The cells consist of approx. 90% lymphocytes and 10% monocytes.

Stimulation of Interleukin 1 from Human Mononuclear Cells in Vitro:

10 µl DMSO/water (1:10, v/v), containing the test compound, was added to 480 µl of a suspension, containing $5 \times 10^6$ mononuclear cells. The synthesis of IL-1 was stimulated by the addition of 10 µl DSMO/water (1:10, v/v), containing 0.5 µg LPS (Salmonella abortus equi, Sigma). After incubation at 37° C. for 18 hours, the samples were cooled to 0° C. and centrifuged for 1 min. in a table centrifuge. 25 µl aliquots for the supernatant were assayed for IL-1 alpha activity using a commercially available 125-J-IL-1-alpha radioimmunoassay Kit (Amersham/UK), and for IL-1 beta in a similar way using the specific test kit. Control experiments were performed as described without test compound, or with cycloheximide as a test compound.

BRIEF DESCRIPTION OF THE DRAWING

The effect of compound 4 as inhibitor of LPS stimulated IL-1 alpha (Approx. $IC_{50}=200–300$ nmol/l), is shown in FIG. 1.

Compound 4 as representative example of the compounds of the present invention inhibits LPS stimulated IL-1 alpha release from human mononuclear cells in vitro.

Figure 1:
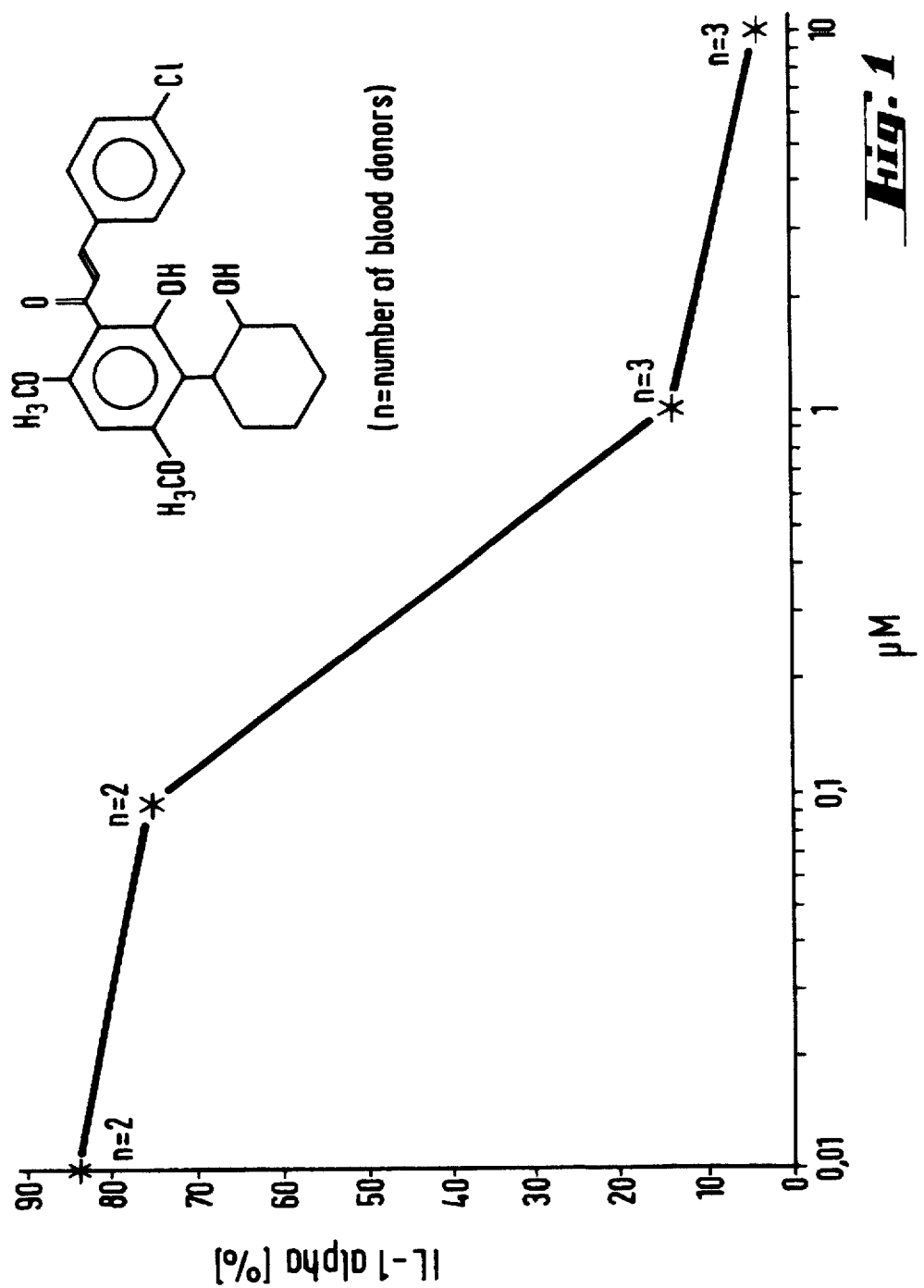

Compounds of the instant application are prepared as described below:

EXAMPLE 5

Preparation of 1-(2,4,6-Trimethoxyphenyl) cyclohexene:

An example of formula V wherein $R_3$=4,6-dimethoxy, $R_2$=$CH_3$.

2,4,6-Trimethoxybromobenzene (1 eqvt.) was taken in a flame dried 3-necked flask under nitrogen. Dry tetrahydrofuran (THF) (983 ml) was added and the reaction mixture was cooled to −30° C. n-BuLi (1.3 eqvt.) in hexane (commercial) was added dropwise and after the addition the reaction mixture was stirred for 30 min. Thin layer chromatographic examination at this stage indicated completion of metallation reaction. Cyclohexanone (1.1 eqvt.) diluted with equal volume of dry THF was added to the reaction mixture at −30° C. and the reaction mixture was stirred for another one hour at −30° C. and later allowed to come to room temperature. Water (150 ml) was added and extracted with ethyl acetate. The ethyl acetate layer was dried over anhydrous sodium sulfate and concentrated. The residue was taken in dichloromethane and stirred for 30 min. with catalytic amount of p-toluenesulphonic acid (9 g). The dichloromethane layer was washed with sodium bicarbonate solution followed by water and dried. The residue was crystallized from Diisopropylether to give the title compound; m.p. 127° C., Yield: 64.7%.

EXAMPLE 6

Preparation of Trans-(±)-2-(2,4,6-Trimethoxyphenyl)cyclohexanol: an example of formula VI wherein $R_2$=$CH_3$, $R_3$=4,6-dimethoxy and $R_4$=OH.

A compound of formula V (from Example 5) (1 eqvt.) was taken along with sodium borohydride (4 eqvt.) and dry THF (2,200 ml). The reaction mixture was cooled to 0° C. under nitrogen and borontrifluoride etherate (5.1 eqvt.) was added dropwise. After the addition was complete, the temperature was raised to 50° C. and stirred for 30 min. The reaction mixture was cooled to room temperature and water was added dropwise to destroy excess diborane. The organoborane was oxidized by simultaneous addition of 30% $H_2O_2$ (248 ml) and 3M NaOH (248 ml) solution. After the addition, the reaction mixture was heated at 50° C. for 3 hours. After completion of oxidation, the reaction mixture was diluted with water and extracted with ethyl acetate. The ethyl acetate layer was dried and concentrated. The curde product was purified by flash chromatography on silica gel using 10% ethyl acetate in pet. ether; m.p. 123° C., Yield: 52%.

EXAMPLE 7

Preparation of Trans-(±)-1-[3-(2-Acetoxy) cyclohexyl-2,4,6-trimethoxy|phenyl-1-ethanone: Formula VII wherein $R_3$-4,6-dimethoxy, $R_2$=$CH_3$ and $R_4$=O—CO—$CH_3$ The product from Example 6 (1 eqvt.) was taken in dry methylene chloride (1520 ml). Acetic anhydride (25 eqvt.) and phosphoric acid (152 ml) were added and stirred at room temperature for one hour. The reaction mixture was worked up by adding sodium carbonate solution until the reaction mixture was alkaline and extracted with dichloromethane. The organic layer was thoroughly washed with water and dried. The crude product after removal of the solvent was crystallized from pet. ether; m.p. 87° C., Yield: 84%.

EXAMPLE 8

Preparation of Trans-(±)-1-[3-(2-Acetoxy) cyclohexyl-4,6-dimethoxy-2-hydroxy|phenyl-1-ethanone: Formula VII wherein $R_2$=H, $R_3$=4,6-dimethoxy and $R_4$=O—CO—$CH_3$ The product from Example 7 (1 eqvt.) was taken in dry dichloromethane (5.450 ml) and cooled to 0° C. Borontribromide (1.1 eqvt.) was added with a syringe and stirred at 0° C. for one hour. Water was added carefully and the product was extracted with ethyl acetate, washed with water, and dried over anhydrous sodium sulfate. The crude product was crystallized from ethyl acetate; m.p. 151° C., yield: 70–71%.

EXAMPLE 9

Preparation of Trans-(±)-2-[3-Acetyl-4,6-dimethoxy-2-hydroxy|phenylcyclohexanol: Formula VII wherein $R_2$=H, $R_3$=4,6-dimethoxy, and $R_4$=OH.

The product from Example 8 (1 eqvt.) was stirred under nitrogen atmosphere with methanolic potassium hydroxide solution (20 eqvt., MeOH:water::3:1) for six hours. The reaction mixture was acidified with dil. HCl and the precipitate was filtered off, washed, dried and crystallized from ethylacetate; m.p. 161° C., Yield: 88–89%.

EXAMPLE 10

Preparation of Trans-(±)-2-[4,6-Dimethoxy-2-hydroxy-3-(3-(4-chlorophenyl)prop-2-(E)-enoyl)| phenylcyclohexanol: Formula II wherein $R_1$=4-chlorophenyl, a=another bond, $R_2$=H, $R_3$=4,6-dimethoxy and $R_4$=OH.

The product from Example 9 (1 eqvt.) was stirred with 4-chlorobenzaldehyde (3 eqvt.) and 10% alcoholic sodium hydroxide (30 eqvt.) at room temperature for 24 hours. The reaction mixture was acidified with the dil. HCl at 0° C. to pH 5 and the orange precipitate was collected by filtration. Recrystallized from ethyl alcohol; m.p. 221° C., yield: 60%.

EXAMPLE 11

Preparation of Trans-(±)-2-[4,6-Dimethoxy-2-hydroxy-3-(3-(4-chlorophenyl)propanoyl)| phenylcyclohexanol: Formula II wherein $R_1$=4-chlorophenyl, a=no bond, $R_2$=H, $R_3$=4,6-dimethoxy and $R_4$=OH.

The product from Example 10 was stirred with 10% pd/c (5 mol %) in ethyl alcohol and under hydrogen overnight. The catalyst was filtered off and the solvent concentrated to give the product; m.p. 190° C., Yield: 90%.

EXAMPLE 12

An Alternative Preparation of Trans-(±)-2-[2,4,6-trimethoxy)phenylcyclohexanol: Formula VI wherein $R_2$=$CH_3$, $R_3$=4,6-dimethoxy and $R_4$=OH.

2,4,6-Trimethoxybenzene (1 eqvt.), cyclohexene oxide (1.5 eqvt.) and dry dichloromethane (840 ml) were taken in 3-necked r.b flask equipped with a stirrer. The reaction mixture was cooled to −78° C. and aluminum chloride (1.5 eqvt.) was added in small portion over a period of one hour. The stirring was continued for an additional period of three hours. The reaction mixture was worked up by addition of water and extracted with ethyl acetate. The crude product was crystallized from petroleum ether; m.p. 123° C., Yield: 63–64%.

EXAMPLE 13

Resolution of (±)-trans-2-(2,4,6-trimethoxy) phenylcyclohexanol: a Compound of Formula VI Wherein $R_2$=H, $R_3$=4,6-dimethoxy and $R_4$=OH.

(±) trans-2-(2,4,6-trimethoxy)phenylcyclohexanol (50.0 g; 0.18797 mol), 3-nitrophthalic anhydride (26.399 g; 0.18797 mol) and pyridine (42.18 ml; 2.78×0.18797 mol) were heated at 100° under $N_2$ atmosphere for three hours. Reaction mixture was cooled to 0° C., neutralized with 2N HCl and the product obtained extracted with chloroform. The residue after evaporation of solvent was crystallized from methanol (400 ml) to give the crystals of compound of the formula VI, wherein $R_4$ is 3-nitrophthalyloxy (59.0 g; m.p. 198°–200°). The hemi acid (0.1285 mol) was treated with (+) cinchonine (37.85 g; 0.1285 mol) in methanol (250 ml) on steam bath for 30 minutes. Solvent was removed at the reduced pressure and the residual salt [96.5 g, OR (+) 84.75° (Hg, 578)] crystallized from ethyl acetate pet. ether (1:1 1400 ml) to afford the crystals (45.0 g; OR (+) 75.11° (Hg 578) and another liquor [50.0 g; OR (+) 97.30° (Hg, 579)].

The crystals (45.0 g) on further crystallizations (thrice) from ethyl acetate-pet. ether afforded enriched cinchonine salt [31.0 g, OR (+) 71.08° (Hg, 578)]. The enriched salt on treatment with 2N HCl at 0° gave the resolved (–) compound of the formula VI, wherein $R_4$ is 3-nitrophthalyloxy [16.1 g; OR (–) 37.15° (Hg, 578). The hemi acid on hydrolysis with 7.5% KOH solution in methanol-water (1:2, 5878 ml) at reflux temperature, followed by crystallization of the product from ethyl acetate-pet. ether (24:160 ml) yielded (–)-trans-2-(2,4,6-trimethoxy)phenylcyclo-hexanol [7.0 g; OR (–) 43.430 (Hg, 578)].

The mother liquor (50.0 g) was treated with 2N HCl at 0° and the product was subjected to crystallizations (thrice) from ethyl acetate-pet. ether to give the crystals of the resolved (+) compound of formula VI; wherein $R_4$ is 3-nitrophthalyloxy [15.1 g; OR (+) 35.65° (Hg, 578)]. The hemi acid on hydrolysis with 7.5% KOH solution in methanol-water (1:2; 548.5 ml) at reflux temperature for 60 hours followed by crystallization of the product from ethyl acetate-pet. ether (25:150 ml) yielded (+) trans-2-(2,4,6-trimethoxy)phenylcyclohexanol [7.24 g; OR (+) 42.30° (Hg, 578)].

We claim:
1. Compounds of the formula I

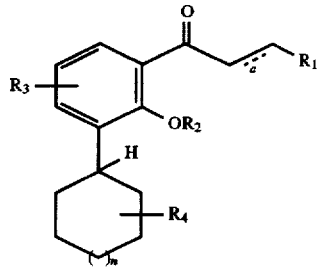

(I)

wherein $R_1$ denotes $C_1$–$C_6$-alkyl, substituted $C_1$–$C_6$-alkyl, C(O) O-1-$C_1$–$C_4$-alkyl, C(O)OH, or the residue

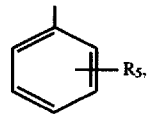

wherein $R_5$ is one, two, three, or four residues which are independent of each other and are selected from H, $C_1$–$C_6$-alkyl, substituted $C_1$–$C_6$-alkyl, hydroxy, $C_1$–$C_6$-alkoxy, carboxy, cyano, NHC(O)$C_1$–$C_3$-alkyl, —O$C_1$–$C_3$-alkyl-phenyl, —OCH$_2$—O—, $C_1$–$C_4$-alkyl—O—$C_1$–$C_4$-alkyl, —O—C(O)—$C_1$–$C_4$-alkyl, —C(O)—O—$C_1$–$C_4$-alkyl, halogen, amino, nitro, —NH—$C_1$–$C_4$-alkyl, —N—($C_1$–$C_4$-alkyl)$_2$, and —$C_1$–$C_4$-alkyl-$R_6$ wherein $R_6$ is a residue selected from

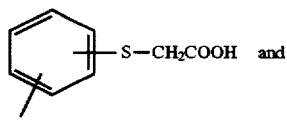

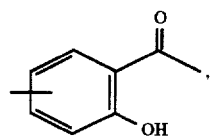

and $R_2$ is H, $C_1$–$C_6$-alkyl, —C(O)—$C_1$–$C_6$-alkyl;

$R_3$ is one, two, or three residues which are independent of each other and selected from H, $C_1$–$C_6$-alkyl, —C(O) —$C_1$–$C_6$-alkyl, —C(O)—O—$C_1$–$C_6$-alkyl, OH, O—$C_1$–$C_6$-alkyl, —O—C(O)—$C_1$–$C_6$-alkyl, and halogen;

$R_4$ is H, —OH, —O—$C_1$–$C_6$-alkyl, —O—C(O)—$C_1$–$C_6$-alkyl, —C(O)—OH, —C(O)—O—$C_1$–$C_6$-alkyl, O—C(=O)—($C_1$–$C_4$-alkyl)-NH$_2$,

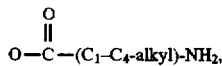

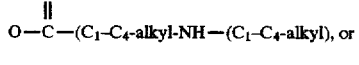

n=0, 1 or 2, and a represents an optional additional single bond, with the proviso that at least one of $R_1$, $R_2$, $R_3$, or $R_4$ is a carboxylic acid ester substituent.

2. Compounds as claimed in claim 1, wherein said compounds have the formula II

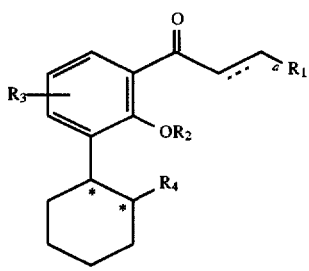

(II)

wherein $R_1$, $R_2$, $R_3$, $R_4$ and a are as defined in claim 1.

3. Compounds of formula I as claimed in claim 1, in which $R_5$ denotes H, $C_1$–$C_6$-alkyl, substituted $C_1$–$C_6$-alkyl, hydroxy, $C_1$–$C_3$-alkoxy, halogen, or $C_1$–$C_4$-alkyl-$R_6$ wherein $R_6$ stands for

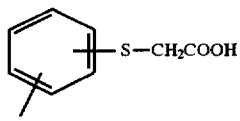

$R_4$ denotes H, OH or

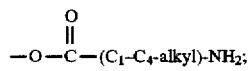

and a denotes an optional additional bond.

4. A process for the production of compounds of the formula I as claimed in claim 1 which comprises converting a compound of the formula V

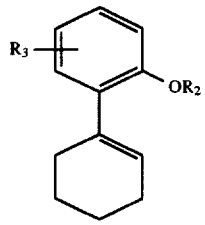

(V)

A) into a compound of the formula VI, $R_4$ denoting OH

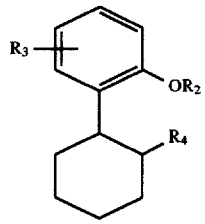

(VI)

by treatment with a borane-solvent-complex followed by oxidation, or

B) treating a compound of formula V with a peracid and treating the epoxide thus produced with a hydride reagent to obtain a compound of formula VI, or C) producing the compound of formula VI by condensation of a suitable arene with cyclohexene oxide in the presence of an acid catalyst, and D) treating a compound of the formula VI with acetic anhydride and a mineral acid to give a compound of the formula VII,

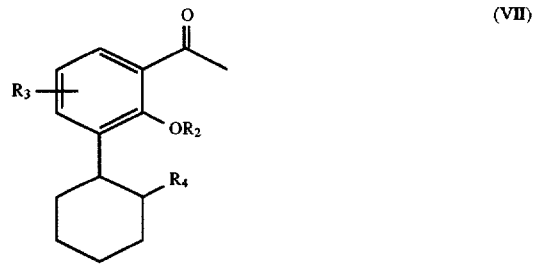

(VII)

wherein $R_2$ is methyl and $R_4$ is O—C(O)—Me, and

E) demethylating a compound of formula VII as described under D) by treatment with a Lewis acid or a demethylating agent to give a compound of formula VII wherein $R_2$ denotes H and $R_4$ denotes OC(O)Me, and F) producing a compound of formula VII wherein $R_2$ denotes H and $R_4$ denotes OH by treatment of a compound produced under E) with dilute alkali, and G) converting the compound of formula VII into a compound of formula I wherein a is an additional bond by treatment with an aldehyde in the presence of a base, or producing a compound of formula I wherein a is not an additional bond by hydrogenation of the compound of formula I wherein a is an additional bond, $R_1$, $R_2$, and $R_3$, where not otherwise explained explicitly, having the meanings as defined in claim 1.

5. A pharmaceutical composition for the treatment of inflammatory conditions containing an effective amount of at least one compound of the formula I as claimed in claim 1 together with a pharmaceutically acceptable carrier.

6. A method for the treatment of inflammatory conditions which comprises administering a pharmaceutical composition as claimed in claim 5 to a host in need of such treatment.

7. A method as claimed in claim 6 for the treatment of chronic inflammatory conditions.

8. A method for the treatment of inflammatory conditions which comprises administering an effective amount of at least one compound of the formula I as claimed in claim 1 to a host in need of such treatment.

9. A method as claimed in claim 8, for the treatment of chronic inflammatory conditions.

* * * * *